(12) United States Patent
Miehlke et al.

(10) Patent No.: US 6,387,131 B1
(45) Date of Patent: May 14, 2002

(54) KNEE PROSTHESIS COMPRISING A TIBIAL WEDGE

(75) Inventors: Rolf K. Miehlke, Munster (DE); Jean-Louis Jermann, deceased, late of St.Julien Les Villas (FR), legal representative Janine Jermann

(73) Assignee: Aesculap (FR)

( * ) Notice: Subject to any disclaimer, the term of this patent is extended or adjusted under 35 U.S.C. 154(b) by 0 days.

(21) Appl. No.: 09/547,744

(22) Filed: Apr. 12, 2000

(51) Int. Cl.[7] .................................................. A61F 2/38
(52) U.S. Cl. ............................ 623/20.15; 623/20.16; 623/20.34
(58) Field of Search .......................... 623/20.15, 20.16, 623/20.34, 20.32

(56) References Cited

U.S. PATENT DOCUMENTS

| 4,944,757 A | * | 7/1990 | Martinez | 623/20 |
| 5,047,058 A | * | 9/1991 | Roberts | 623/20 |
| 5,062,852 A | * | 11/1991 | Dorr | 623/20 |
| 5,344,461 A | * | 9/1994 | Philpot | 623/20 |
| 5,387,241 A | | 2/1995 | Hayes | 623/20 |
| 5,458,637 A | | 10/1995 | Hayes | 623/16 |
| 5,480,445 A | * | 1/1996 | Burkinshaw | 623/20 |
| 5,658,341 A | * | 8/1997 | Delfosse | 623/20 |
| 5,938,698 A | * | 8/1999 | Sandoz | 623/11 |

FOREIGN PATENT DOCUMENTS

EP 0 538 987 B1 4/1993

* cited by examiner

Primary Examiner—Paul B. Prebilic
(74) Attorney, Agent, or Firm—Renner, Kenner, Greive, Bobak, Taylor & Weber

(57) ABSTRACT

A knee prosthetic including a tibia part (1), which includes a tibia plate (2) that co-operates with at least one meniscal element by a first side (4), and co-operates with a tibia resection plan by a second side (5), including a tibia pin (3) connected with the tibia plate (2), which penetrates into the tibia to fix the tibia part (1) into it; and at least one compensating tibia block (6), which fits flatly between the second side (5) of the tibia plate (2) and the tibia itself, in order to compensate for a lack or absence of local bone tissue between the tibia and the resection plan. This tibia block (6) also co-operates with said tibia part (1) by way of complementary fixating means (10, 11) that are implemented on the tibia block (6) and tibia part, wherein the complementary fixating means are of the pin (10) and hole (11) type and are implemented on the tibia block and the base (9) of the tibia pin.

14 Claims, 1 Drawing Sheet

KNEE PROSTHESIS COMPRISING A TIBIAL WEDGE

BACKGROUND OF THE INVENTION

The present invention relates to knee prosthetics of the type, including a tibia part, which will be fixed to a tibia that has been prepared. It includes a tibia plate, which will co-operate with at least one meniscal element by a first side, and co-operate with a resection plan of the tibia by a second side. It includes a tibia pin as part of the tibia plate, which will penetrate inside the tibia so that the tibia part can be fixed onto it. It includes at least one tibia block for thickening, which will fit flatly between the second side of the tibia plate and the tibia itself, in order to compensate for a lack of local bone tissue between the tibia and the resection plan. The tibia block co-operates with the tibia plate by way of complementary fixating means, featured on the tibia block and the tibia plate.

Such a compensating tibia block is used when a lack or absence of bone tissue exists underneath the tibia resection plan, and a new resection cannot be carried out, as can sometimes be the case with modifying a single-compartment knee prosthetic or poor bone quality, ie in the case of arthritis.

BRIEF SUMMARY OF THE INVENTION

The aim of the invention is to provide a simple and reliable assembly of the tibia block onto the tibia part of the prosthetic.

To this end, the prosthetic according to the invention is characterised by the complementary fixating means being of the pin and retaining-hole which are held by the tibia block and the base of the tibia pin.

According to the present invention, in the assembly mode the pin is inserted into a hole to ensure the assembly and retaining of the tibia block on the base of the tibia pin.

According to a second aspect of the preferred invention, the pin is featured on the base of the tibia pin and the hole is implemented in the tibia block; this pin may constitute the base of an anchoring ridge in the tibia, connected with the tibia pin.

The pin advantageously features a shrunk shaft, distant from its free extremity, which will receive at least one locking bulge implemented at the opening of the retaining hole.

The complementary fixating means preferably include at least one ridge to allow for the deformation of the material in order to achieve an elastic clamping of the pin and the hole and/or the penetration of the pin in the hole. This ridge can extend either along the hole on at least part of its length and a small distance away from it in order to define a flexing plate with it, or along the pin on at least part of its length and up to its free extremity so as to define two flexing tongues.

The pin and the hole can have a general direction which follows the axis of the tibia pin.

In order to assemble the tibia block on either side of the tibia pin, the tibia pin includes part of said fixating means, for instance two pins which are symmetrical with regard to the median antero-posterior plane of the tibia pin.

The complementary fixating means are, for instance, placed so that the tibia block assembles on the base of the tibia pin by a sliding movement perpendicular to the sides of the tibia plate and parallel to the axis of the tibia pin. A variation involves the complementary fixating means placed so that the tibia block assembles on the base of the tibia pin by a sliding movement, parallel to the sides of the tibia plate and perpendicular to the axis of the tibia pin.

BRIEF DESCRIPTION OF THE SEVERAL VIEWS OF THE DRAWINGS

The invention will be understood with reading the following description complement and referring to the Figures, which form part of the description, and within which.

Figure 1:
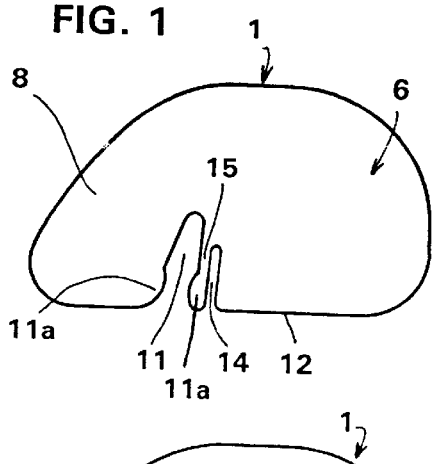
FIGS. 1 and 2 are underneath views respectively representing the tibia block and the tibia part of a knee prosthetic according to a preferred implementation of the invention.

The tibia part 1 of a knee prosthetic according to a preferred implementation of the invention is represented in the Figures.

It is known that tibia part 1, includes a tibia plate 2 and a tibia pin 3, connected with the plate and assembled to it by any appropriate means or forming a single piece with it.

The tibia plate 2 co-operates by way of its upper side 4, with at least one prosthetic meniscal element (not represented) and, by way of its underside 5, with a resection plan P of the tibia (not represented). The tibia pin 3 penetrates the tibia to enable the fixation of the tibia part 1 onto it.

Figure 3:
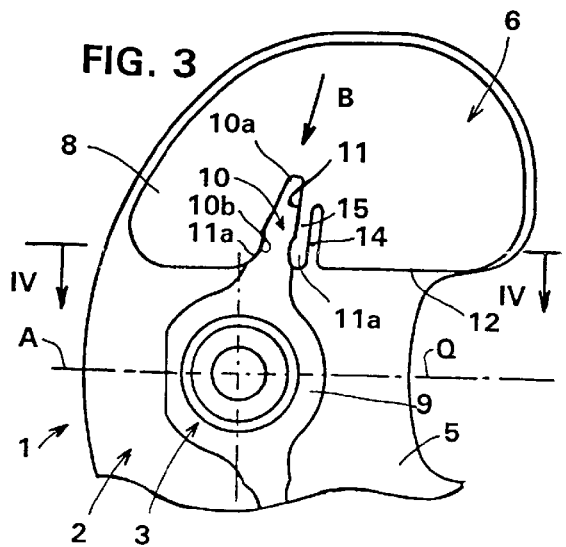
FIG. 3 is a view similar to FIGS. 1 and 2 and represents the tibia block in place, underneath and against the tibia plate, with the tibia plate being only partially represented.
Figure 4:
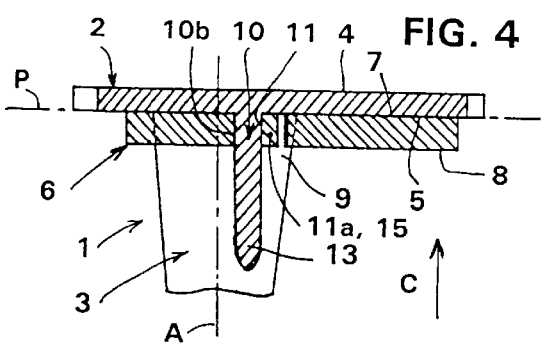
FIG. 4 is a vertical split view which follows the IV—IV line of FIG. 3.
Figure 5:
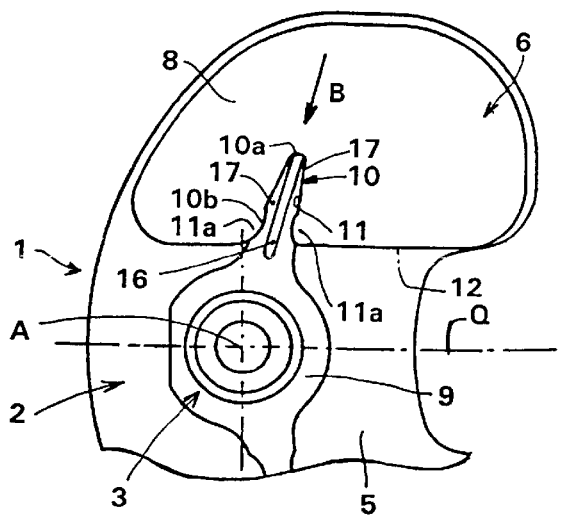
FIG. 5 is a view similar to FIG. 3 and represents a variation of the implementation.

As indicated previously, the prosthetic includes at least one compensating tibia block 6, which will fit flatly between the tibia plate 2 and the resection plan P, to compensate for absence or lack of bone tissue under the resection plan P, represented on FIG. 4 as a dotted line. The upper side 7 of the tibia block 6 is in contact against the underside 5 of the tibia plate 2 and the underside 8 of the tibia block 6 is in contact against the tibia, underneath the resection plan P, which coincides with the underside 5 of the tibia plate. As represented in FIGS. 3 and 5, the curved external shape of the block 6 is slightly retreated from the associated curved shape of the tibia plate, for the assembled position.

The tibia block 6 is mounted on the base 9 of the tibia pin by way of complementary fixating means, which are implemented on the tibia block 6 and the base 9 of the tibia pin 3, and comprise of a pin 10 and a hole 11.

In the Figures shown, the pin 10 is implemented on the base 9 of the tibia pin 3 and the hole 11 is implemented in the tibia block 6. This set-up is preferred for positional reasons as the internal edge 12 of the block 6 is relatively close to the tibia pin 3 and could hardly include a pin 10 that fits a hole 11, implemented in the tibia pin which would in this case, offer a diminished mechanical stress tolerance.

The pin 10 features a shrunken shaft 10b, distant from its free extremity 10a, which will receive at least one locking bulge 11a implemented at the opening of the hole 11, in order to retain the pin 10 inside the hole 11. In the examples represented, two bulges 11a are implemented on either sides of the entrance shaft in hole 11.

The pin 10 and the hole 11 have elongated and complementary shapes, with a tight fitting tolerance for clasping. These elongated and complementary shapes enable a precise and correct angular positioning of the block on the tibia part. In the radial direction, the relative position is defined by the pin reaching the end of the hole. In the examples represented, the pin 10 is sharpened from its shaft 10b so as to feature a rounded point at its free extremity 10a, and the hole 11 features a complementary shape, from the bulges 11a onwards.

Figure 2:
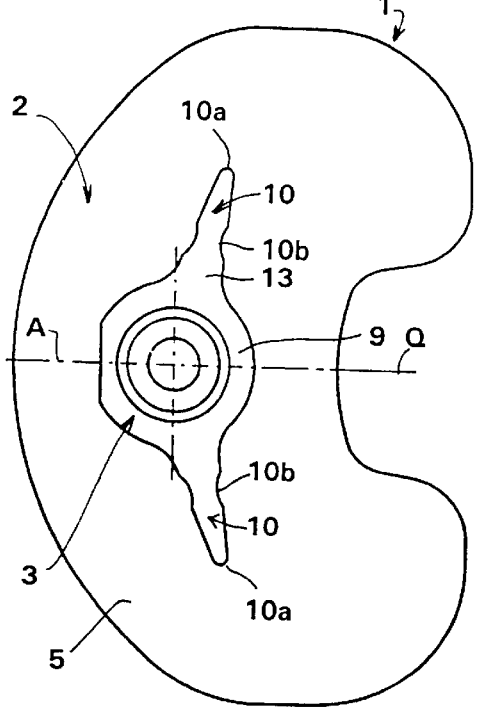

The tibia pin 3 includes two pins 10, which are located symmetrically compared with the median pre-posterior plan Q, which itself intersects the axis A of the pin 3 (FIGS. 2, 3 and 5). The implementation of two pins 10 enables the selective positioning of the tibia block 6 either to the left or to the right.

Furthermore, the pins 10 constitute the base for linking the tibia plate 2 with anchoring ridges 13, which form an integral part of the tibia pin 3 and which will penetrate the tibia. The ridges 13 are shaped like a whistle in order to blend with the body of the tibia pin 3, which is some distance away from the tibia plate 2 (FIG. 4).

As represented on FIGS. 2, 3 and 5, the general direction of the pins 10 and the hole 11 of the block 6 intersects with the axis A of the tibia pin 3.

As represented by the arrow B (FIGS. 3 and 5), the tibia block 6 co-operates with the tibia pin 3 by way of the pin 10, by a sliding movement following a direction which is transversal and parallel to the general direction of the pin 10 and the hole 11, parallel with the sides 4 and 5 of the tibia plate 2 and perpendicular to the axis A of the tibia pin. Alternatively, the tibia block 6 co-operates with the tibia pin 3 by way of the pin 10, by a sliding movement following a direction which is transversal and parallel to the general direction of the pin 10 and the hole 11, and which is perpendicular with the sides 4 and 5 of the tibia plate 2 and parallel to the axis A of the tibia pin, as represented by the arrow C (FIG. 4).

It is necessary to be able to alter the shape of the material in order to ensure that an elastic clasping of the pin 10 and the hole 11 is achieved, and in the case of a transversal set-up, in order for the pin 10 to progress through the entrance bulges 11a of the hole 11.

In the implementation represented in FIGS. 1 to 4, the shape of the material can be altered by way of a ridge 14 of an appropriate width implemented on at least one side of the hole 11, running from the edge 12 of the block on at least part of the length of hole 11 and a small distance away from it which defines a flexing plate or tongue 15.

When the pin 10 penetrates the hole 11, the plate 15 flexes towards the ridge 14 to elastically widen the space between the entrance bulges 11a of the hole 11. In the case of a transversal set-up, the largest part of the pin 10 which is immediately before the shaft 10b, traverses the entrance of the hole. The plate 15 then flexes back by way of its elasticity into a locking position so that the bulges 11a co-operate with the shaft 10b.

The variation represented in FIG. 5 only differs from the implementation method represented in FIGS. 1 to 4 by the means employed to achieve the alteration of the shape of the material.

In this implementation method, it is the pin 10 which features a longitudinal ridge 16, from its link with the tibia pin 3 and on an appropriate height. The ridge 16 is of an appropriate width and extends from the free extremity 10a to beyond the shaft 10b, following the general direction of the pin 10. The central ridge 16 defines a flexing plate or tongue 17. When the pin 10 penetrates the hole 11, the plates 17 flex towards the central ridge 16.

In the case of an axial positioning of the tibia block 6, following the arrow C of FIG. 4, the flexing of the plates 15 and 17 is not necessarily large as the aim is only to ensure that the pin 10 is clasped by the wall of the hole. However, in the case of a transversal positioning, following the arrow B of FIGS. 3 and 5, the flexing must be larger as the aim is to ensure that the widest part of the pin 10, situated before the shaft 10b traverses the bulges 11a.

The invention is not limited to the implementation methods which have been described. Many variations may be conceived without however exiting its domain.

What is claimed is:

1. A knee prosthetic including a tibia part, which includes a tibia plate that cooperates with at least one meniscal element by a first side, and cooperates with a tibia resection plan by a second side, including:
    a tibia pin connected with the tibia plate which penetrates into the tibia to fix the tibia part into it; and
    at least one compensating tibia block which fits flatly between the second side of the tibia plate and the tibia itself, in order to compensate for a lack or absence of local bone tissue between the tibia and the resection plan, wherein said tibia block also cooperates with said tibia part by way of complementary fixating means that are implemented on the tibia block and tibia part, wherein the complementary fixating means are of the pin and hole type and are implemented on the tibia block and the base of the tibia pin, wherein the fixating means include at least one ridge which allows for the alteration of the shape of the material to achieve an elastic clasping between the hole and the pin, and/or the penetration of the pin in the hole, and wherein a ridge extends in the pin, along and on at least part of its length until its free extremity in order to define two flexing tongues.

2. A knee prosthetic including a tibia part, which includes a tibia plate that cooperates with at least one meniscal element by a first side, and cooperates with a tibia resection plan by a second side, including:
    a tibia pin connected with the tibia plate which penetrates into the tibia to fix the tibia part into it; and
    at least one compensating tibia block which fits flatly between the second side of the tibia plate and the tibia itself, in order to compensate for a lack or absence of local bone tissue between the tibia and the resection plan, wherein said tibia block also cooperates with said tibia part by way of complementary fixating means that are implemented on the tibia block and tibia part, wherein the complementary fixating means are of the pin and hole type and are implemented on the tibia block and the base of the tibia pin and wherein the pin and hole complementary fixating means features at least one locking bulge.

3. A knee prosthetic including a tibia part, which includes a tibia plate that cooperates with at least one meniscal element by a first side, and cooperates with a tibia resection plan by a second side, including:
    a tibia pin connected with the tibia plate which penetrates into the tibia to fix the tibia part into it; and
    at least one compensating tibia block which fits flatly between the second side of the tibia plate and the tibia itself, in order to compensate for a lack or absence of local bone tissue between the tibia and the resection plan, wherein said tibia block also cooperates with said tibia part by way of complementary fixating means that are implemented on the tibia block and tibia part, wherein the complementary fixating means are of the pin and hole type and are implemented on the tibia block and the base of the tibia pin, wherein the fixating means include at least one ridge which allows for the alteration of the shape of the material to achieve an elastic clasping between the hole and the pin, and/or the penetration of the pin in the hole, and wherein a ridge extends along the hole on at least one side, and on at least part of its length and a small distance away from it, in order to define a flexing tongue.

4. A knee prosthetic according to claim 1, wherein the pin constitutes the base of a ridge anchoring within the tibia and which is connected with the tibia pin.

5. A knee prosthetic according to claim 1, wherein the pin features a shrunken shaft some distance away from its free extremity, which will receive at least one locking bulge implemented at the entrance of the hole.

6. A knee prosthetic according to claim 1, wherein the fixating means include at least one ridge which allows for the alteration of the shape of the material to achieve an elastic clasping between the hole and the pin, and/or the penetration of the pin in the hole.

7. A knee prosthetic according to claim 6, wherein a ridge extends along the hole on at least one side, and on at least part of its length and a small distance away from it, in order to define a flexing tongue.

8. A knee prosthetic according to claim 6, wherein a ridge extends in the pin, along and on at least part of its length until its free extremity in order to define two flexing tongues.

9. A knee prosthetic according to claim 1, wherein the pin and the hole have a general direction which intersects the axis A of the tibia pin.

10. A knee prosthetic according to claim 1, wherein the tibia pin includes part of the fixating means, symmetrically compared to the median antero-posterior plan of the tibia pin.

11. A knee prosthetic according to claim 1, wherein the complementary fixating means are implemented so that the tibia block slides onto the base of the tibia pin, by a movement (C) perpendicular to the sides of the tibia plate and parallel to the axis (A) of the tibia pin.

12. A knee prosthetic according to claim 2, wherein said at least one locking bulge is implemented in the hole and cooperates with a shrunken shaft of said pin.

13. A knee prosthetic according to claim 2, wherein the pin is implemented on base of the tibia pin and the hole is implemented in the tibia block.

14. A knee prosthetic according to claim 13, wherein the pin constitutes the base of a ridge anchoring within the tibia and which is connected with the tibia pin.

* * * * *